(12) United States Patent  
Patrikakis

(10) Patent No.: US 6,230,348 B1  
(45) Date of Patent: May 15, 2001

(54) NECK REST

(76) Inventor: Pano Patrikakis, 25 Cosburn Ave., Apt. 1101, Toronto, Ontario (CA), M4K 3Y4

( * ) Notice: Subject to any disclaimer, the term of this patent is extended or adjusted under 35 U.S.C. 154(b) by 0 days.

(21) Appl. No.: 09/366,769

(22) Filed: Aug. 4, 1999

(51) Int. Cl.[7] .................................................. A47G 9/00
(52) U.S. Cl. ........................................... 5/636; 5/637
(58) Field of Search ............................ 5/630, 636, 637, 5/638

(56) References Cited

U.S. PATENT DOCUMENTS

| | | | |
|---|---|---|---|
| 4,345,347 | * 8/1982 | Kantor | 5/636 X |
| 5,026,315 | * 6/1991 | Chap | 5/636 X |
| 5,261,134 | * 11/1993 | Matthews | 5/655 |
| 5,661,861 | * 9/1997 | Matthews | 5/633 |
| 6,038,720 | * 3/2000 | Matthews et al. | 5/636 |

\* cited by examiner

*Primary Examiner*—Terry Lee Melius  
*Assistant Examiner*—Fredrick Conley

(57) ABSTRACT

The present invention is directed to a neck rest moulded from a foamed material and having a rear pillow portion of a generally tubular configuration and two generally parallel laterally extending support sections extend at right angles from the front face at each end of said pillow portion. The opposing inner surfaces of the support are curved to form a keyhole shaped space between the support sections sized to permit the neck rest to comfortable fit around a person's neck without feeling yoked. The top surfaces and bottom surfaces of said support sections are preferably flat with rounded, the top surface of the pillow portion is higher than the top surfaces of the support sections and is curved to fit comfortable against the nape of the users neck. A flocking material is applied to the exterior surfaces of the neck rest.

8 Claims, 3 Drawing Sheets

NECK REST

FIELD OF THE INVENTION

The present invention relates to a pillow or neck rest for use to support a user's neck. In particular, the present invention provides a neck and head support that is designed to caress the neck in a comfortable manner without asphyxiating the individual or causing sweat or perspiration.

BACKGROUND OF THE INVENTION

There are hundreds of designs for pillows or neck rests primarily alleging a thearaputic or medical (recuperation) purposes. Most of these devices are cumbersome to use since they are designed to hold in place an injured neck. Another type of neck rest that has been used is inflatable. It can be difficult to use since it takes a lot out of a healthy person to inflate it and it is quite time consuming to deflate it. For this reason the inflatable neck rest is rather impractical since an older person would not be able to inflate it without feeling dizzy or out of breath and similarly go through the time consuming process of deflating it in order to store away.

These designs ignore the real need of people who would gladly use a neck rest support which is NOT awkward, bulky, unappealing, heavy and impractical at various occasions including while driving or riding in a car or flying in an airplane. Some of the prior art designs include U.S. Pat. No. 5,257,429; U.S. Pat. No. 5,220,700; U.S. Pat. No. 5,129,705; U.S. Pat. No. 5,778,469; U.S. Pat. No. 5,546,619; U.S. Pat. No. 5,457,832; U.S. Pat. No. 5,339, 472 and U.S. Pat. No. 5,261,134.

There is a need for a pillow or neck rest that is moisture—water-proof fabrication; retractability, cushiony; light weight—portability; easy to use; totally in sync with environmental and health issues; non-allergenic and provide neck support.

SUMMARY OF THE INVENTION

It is an object of the present invention to provide neck and head support in a comfortable manner without asphyxiating the individual or causing sweat or perspiration.

It is a further object to provide a cushiony feeling to the neck and head in a comfortable and soothing manner without feeling yoked. Thus the elasticity and retractability property of the item is measurable.

It is a still further object to provide a neck rest that is water-moisture resistant/proof meaning that it does not absorb water or moisture thus making it unsavory and also turning into a sponge.

Another object of the present invention is to provide a light weight design, approximately 150–180 grams or 5.2–6.3 oz enabling the individual to easily carry it along without feeling burdened by its weight.

A still further object is to provide a design that is stable once the individual places it on his neck and does not impede head movements in any direction.

Another object of the present invention is to provide a non-allergenic construction to prevent skin rashes or other health care problems arising from its fabrication material nor does it present any environmental issue or concern.

The present invention is directed to a neck rest having a rear pillow portion of a generally tubular configuration. Two generally parallel laterally extending support sections extend at right angles from the front face at each end of pillow portion. The opposing inner surfaces of the support are curved to form a keyhole shaped space between the support sections sized to permit the neck rest to comfortable fit around a person's neck without feeling yoked. The top surfaces and bottom surfaces of said support sections are preferably flat with rounded edges to provide comfort to the user. The top surface of the pillow portion is higher than the top surfaces of the support sections and is curved to fit comfortable against the nape of the users neck.

The neck rest is moulded from a foamed material, preferably a self-skinning foamed material, which will form an impermeable skin on the exterior surface of the neck rest to provide a neck rest that is water-moisture resistant/proof . A flocking material applied to its exterior surfaces to provide a non-allergenic construction to prevent skin rashes or other health care problems arising from its fabrication material.

BRIEF DESCRIPTION OF THE DRAWINGS

A preferred embodiment of a neck rest according to the present invention is illustrated in the attached drawings in which.

DETAILED DESCRIPTION OF THE PREFERRED EMBODIMENT

Figure 1:
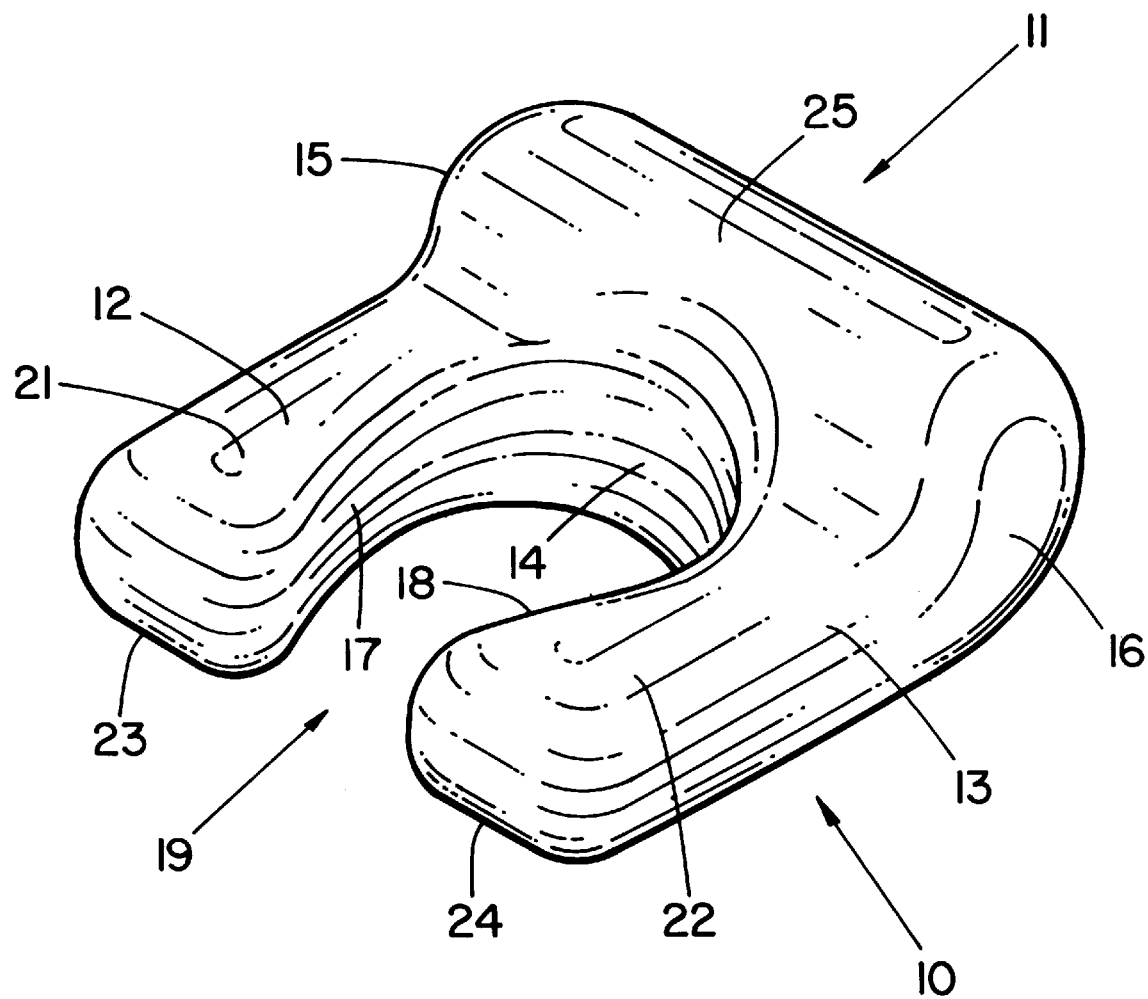
FIG. 1 is a front perspective view of the neck rest of the present invention.
Figure 2:
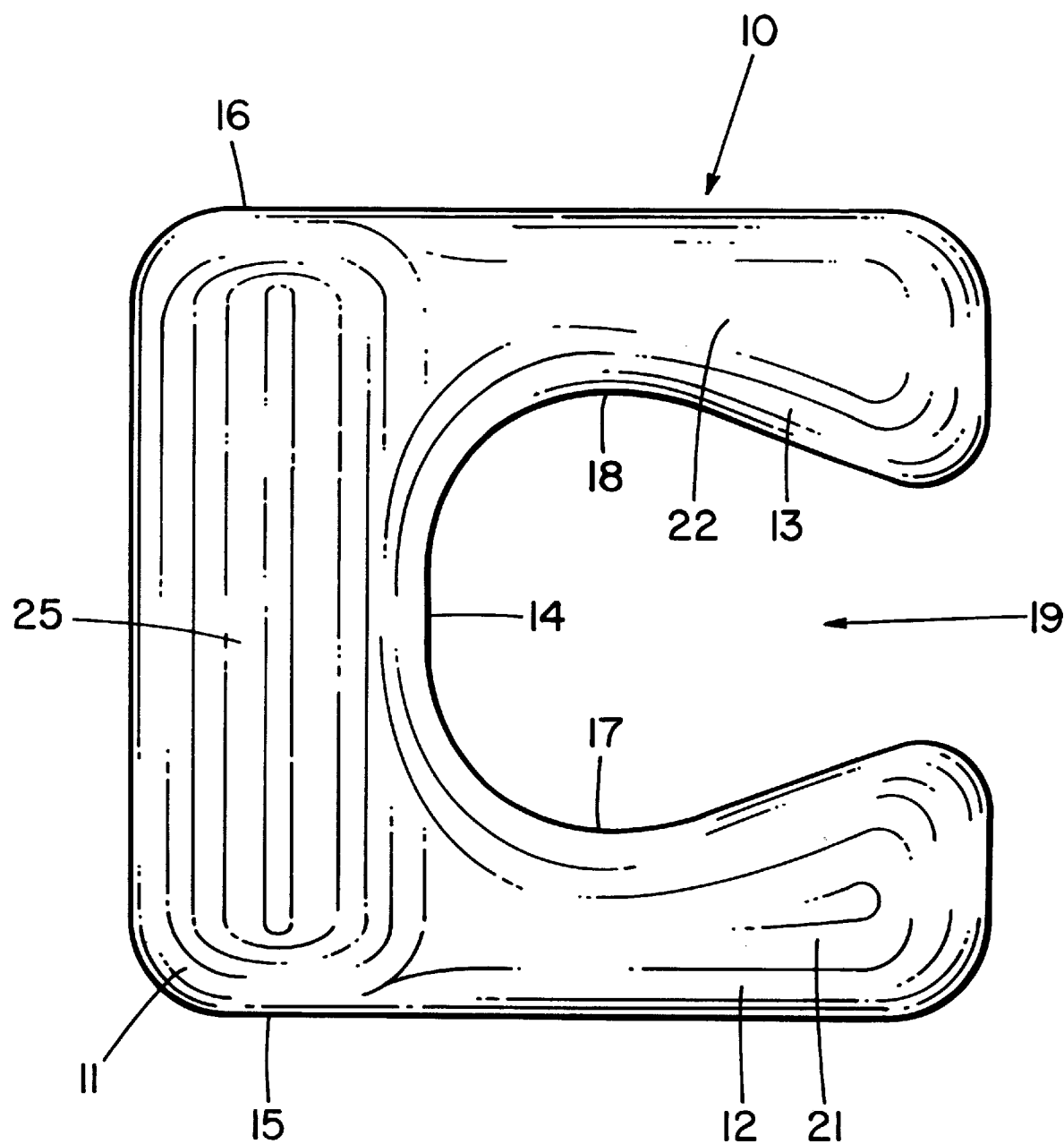
FIG. 2 is a top elevation view of the neck rest of the present invention.
Figure 3:
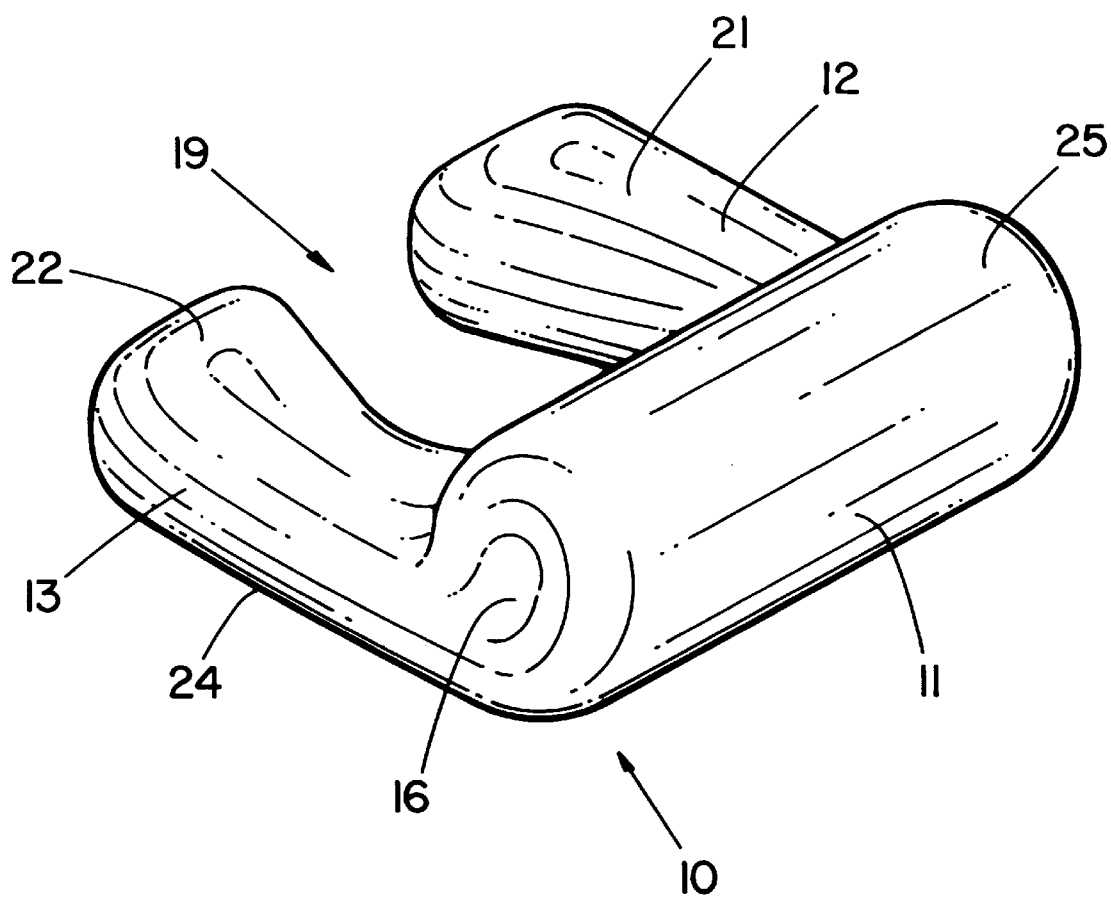
FIG. 3 is a rear perspective view of the neck rest of the present invention.

As illustrated in FIGS. 1 to 3, the neck rest 10 of the present invention has a rear pillow portion 11 having a generally tubular configuration. Two generally parallel laterally extending support sections 12, 13 extend at right angles from the front face 14 at each end 15, 16 of pillow portion 11. The opposing inner surfaces 17, 18 of the support sections 12, 13 are curved to form a keyhole shaped space 19 between the support sections 12,13 sections sized to permit the neck rest to comfortable fit around a person's neck without feeling yoked. The top surfaces 21, 22 and bottom surfaces 23, 24 of said support sections 12, 13 are preferably flat with rounded edges to provide comfort to the user. The top surface 25 of pillow section 11 is higher than the top surfaces 21, 22 of the support sections 12, 13 and is curved to fit comfortable against the nape of the users neck.

In order to improve the water impermeability of the neck rest 10, the neck rest is moulded from a foamed material, preferably a self-skinning foamed material, which will form an impermeable skin on the exterior surface of the neck rest 10. While the selection of the foaming material is well within the knowledge of those of ordinary skill in the art, it is preferred if the foaming material is a polyurethane or polyester most preferably polyurethane.

The moulded neck rest should preferably be formed of a material having the following properties to provide the desired retractability, cushiony feel and light weight:

|  |  | 80 Index | 100 index |
|---|---|---|---|
| Overall Density | lb/cu. ft | 3.4 | 3.4 |
|  | Kg/cu.m | 54.46 | 54.46 |
| Tensile Strength | psi | 10.20 | 18.6 |
| Elongation | % | 143 | 133 |
| Block Tear |  | 1.2 | 1.5 |

-continued

|  |  | 80 Index | 100 index |
|---|---|---|---|
| Indentation Load/Force Deflection |  |  |  |
| @ 25% Deflection | N | 112.40 | 232.80 |
|  | lbf | 25.20 | 52.20 |
| @ 65% Deflection | N | 305.00 | 633.00 |
|  | lbf | 68.39 | 141.90 |
| @ 25% Return | N | 94.60 | 184.20 |
|  | lbf | 21.21 | 41.30 |
| Support Factor |  | 2.70 | 2.70 |
| Recovery |  | 84.13 | 79.12 |
| Compressive Set/Constant Deflection Set |  |  |  |
| @ 50% Deflection | % | 11.30 | 11.20 |
| @ 75% Deflection | % | 10.30 | 8.60 |
| @ 50% Deflection HA | % | 22.40 | 25.30 |
| @ 75% Deflection HA | % | 17.60 | 20.70 |
| Dynamic Fatigue |  |  |  |
| Load loss @ 40% IFD | % | 15.4 | 16.1 |
| Height loss | % | 2.5 | 3.0 |

A preferable material is BASF's Elastoflex™ F 4202 polyurethane flexible foam.

From the mould neck rest 10 has a flocking material applied to its exterior surfaces to provide a non-allergenic construction to prevent skin rashes or other health care problems arising from its fabrication material. The flocking material is preferably selected from cotton, rayon, acrylic, nylon or polyester. To apply the flocking material to the exterior surface of the neck rest an adhesive is applied to the neck rest. The flocking material is then applied over the adhesive by an electrostatic or electrostatic air assist process. The neck rest is then dried and is ready for use. The flocking material aids in giving the neck rest of the present invention a cushiony feel in a comfortable and soothing manner.

The neck rest 10 is placed around the back and side of the neck to provide neck and head support in a comfortable manner without asphyxiating the individual or causing sweat or perspiration. The design is stable once the individual places it on his/her neck and does not impede head movements in any direction. The use of the foam material provides a light weight design, approximately 150–180 grams or 5.2–6.3 oz enabling the individual to easily carry it along without feeling burdened by its weight.

The therapeutic benefits of the neck rest can be enhanced by inserting a thin strip layer of magnetic material into the rear pillow portion and/or the support sections of the neck rest during the moulding process.

While a preferred embodiment of a neck rest according to the present invention has been described in detail it will be appreciated by those skilled in the art that variations may be made thereto without departing from the spirit of the invention or the scope of the appended claims.

What is claimed is:

1. A neck rest to fit around the back and sides of the neck of a person, said neck rest comprising:
    (a) pillow portion of a generally tubular configuration and having first and second ends, front and rear faces and top and bottom edges, said pillow section adapted to support the back of the neck of a person;
    (b) a first lateral support section extending at right angles from the front face of said pillow section adjacent its first end, said first lateral support section having top and bottom surfaces and inner and outer side surfaces, said first lateral support adapted to support one side of the neck of a person;
    (c) a second lateral support section extending at right angles from the front face of said pillow section adjacent its second end, said second lateral support section having top and bottom surfaces and inner and outer side surfaces, said second lateral support adapted to support the other side of the neck of a person;
    (d) the inner surfaces of said first and second lateral support sections are curved to form a keyhole shaped space between the said first and second lateral support sections, said keyhole shaped space sized to permit the neck rest to comfortable and snugly fit around a person's neck without feeling choked;
    (e) said pillow portion being thicker than said first and second lateral support sections wherein the top edge of said pillow portion is higher than the top surfaces of said first and second lateral support sections; and
    (f) said neck rest moulded from a self-skinning, water resistant foam material.

2. A neck rest according to claim 1 wherein the front face of said pillow portion is curved to fit comfortable against the back of the neck.

3. A neck rest according to claim 1 wherein a covering material is applied over the neck rest.

4. A neck rest according to claim 3 wherein the covering material is selected from cotton, rayon, acrylic, nylon or polyester.

5. A neck rest according to claim 1 that is lightweight.

6. A neck rest according to claim 5 that weighs between 150 to 180 grams.

7. A neck rest according to claim 1 wherein the foam material is selected from the group consisting of polyurethane, polyester, polyvinyl or polyethylene.

8. A neck rest according to claim 7 wherein the neck rest is formed from a foamed polyurethane.

* * * * *